United States Patent
Dominguez

(10) Patent No.: US 11,517,744 B1
(45) Date of Patent: Dec. 6, 2022

(54) DEVICE FOR USING ELECTROTHERAPY FOR THE RELIEF OF HEMORRHOID INFLAMMATION

(71) Applicant: Hemotec, LLC, Tampa, FL (US)

(72) Inventor: Yamil Dominguez, Tampa, FL (US)

( * ) Notice: Subject to any disclaimer, the term of this patent is extended or adjusted under 35 U.S.C. 154(b) by 0 days.

(21) Appl. No.: 16/827,603

(22) Filed: Mar. 23, 2020

(51) Int. Cl.
- *A61N 1/05* (2006.01)
- *A61N 1/372* (2006.01)
- *A61N 1/375* (2006.01)

(52) U.S. Cl.
CPC ......... *A61N 1/0512* (2013.01); *A61N 1/3758* (2013.01); *A61N 1/37211* (2013.01)

(58) Field of Classification Search
CPC ... A61N 1/0456; A61N 1/0512; A61N 1/3758
See application file for complete search history.

(56) References Cited

U.S. PATENT DOCUMENTS

| | | | | |
|---|---|---|---|---|
| 4,823,791 A | * | 4/1989 | D'Amelio | A61B 18/14 219/234 |
| 5,676,637 A | * | 10/1997 | Lee | A61H 21/00 601/15 |
| 6,077,257 A | * | 6/2000 | Edwards | A61B 18/12 604/506 |
| 8,123,760 B2 | * | 2/2012 | Blurton | A61F 5/0093 606/119 |
| 8,868,190 B2 | * | 10/2014 | Guez | A61N 1/36007 607/41 |
| 9,700,719 B1 | * | 7/2017 | Dominguez | A61N 1/0512 |
| 2005/0049660 A1 | * | 3/2005 | Croft | A61B 18/1485 607/101 |
| 2005/0228371 A1 | * | 10/2005 | West | A61B 1/31 606/41 |
| 2008/0208188 A1 | * | 8/2008 | Cao | A61N 1/0512 606/41 |
| 2009/0222058 A1 | * | 9/2009 | Craggs | A61N 1/0512 607/41 |
| 2012/0215280 A1 | * | 8/2012 | Peddicord | A61H 19/00 607/48 |
| 2013/0046328 A1 | | 2/2013 | Bourque | |
| 2019/0038446 A1 | | 2/2019 | Takemoto | |

* cited by examiner

*Primary Examiner* — Rex R Holmes
*Assistant Examiner* — Jennifer L Ghand
(74) *Attorney, Agent, or Firm* — Sanchelima & Associates, P.A.; Christian Sanchelima; Jesus Sanchelima

(57) ABSTRACT

A device for hemorrhoid relief that includes a housing assembly and a capsule assembly is disclosed. The housing assembly includes a housing that houses a battery and a communication module. The battery may be recharged through a wireless charging means. Additionally, the communications module allows the device to pair to a mobile device through Bluetooth. The capsule assembly includes a plastic core having two sides. An anode pole and a cathode pole are then coupled to the two sides of the plastic core. The capsule assembly serves a neutral core. The capsule assembly is then inserted into a user's anus. The device then delivers biphasic electrotherapy pulses within the anus to reduce the inflammation of hemorrhoids.

14 Claims, 7 Drawing Sheets

DEVICE FOR USING ELECTROTHERAPY FOR THE RELIEF OF HEMORRHOID INFLAMMATION

BACKGROUND OF THE INVENTION

1. Field of the Invention

The present invention relates to a device for hemorrhoid relief and, more particularly, to a device inserted within a user's anus that generates biphasic electrotherapy pulses.

2. Description of the Related Art

Several designs for hemorrhoid relief have been designed in the past. None of them, however, include a device for hemorrhoid relief that includes a housing assembly and a capsule assembly. The housing assembly includes a housing that houses a battery and a communication module. The battery may be recharged through a wireless charging means. Additionally, the communications module allows the device to pair to a mobile device through Bluetooth. The capsule assembly includes a plastic core having two sides. An anode pole and a cathode pole are then coupled to the two sides of the plastic core. The capsule assembly serves a neutral core. The capsule assembly is then inserted into a user's anus. The device then delivers biphasic electrotherapy pulses within the anus to reduce the inflammation of hemorrhoids. It is known that individuals who suffer from hemorrhoid inflammation often try several methods to reduce the inflammation. These methods may include hemorrhoid cream or other expensive treatment methods that may not be readily available or effective for the individual. Therefore, there is a need for a device that is easily operated by a user through a mobile device in order to provide relief to an individual suffering from hemorrhoid inflammation.

Applicant believes that a related reference corresponds to U.S. patent publication No. US20130046328A1 issued for a hemorrhoid pressure relief device having fluid fill inside a tube made of a supple, soft, and yet highly tensile strong material that produces a gentle support and counter pressure over the hemorrhoid bulge. Applicant believes that another related reference corresponds to U.S. patent publication No. US20190038446A1 issued for a kit for providing pain relief to a user suffering from rectal, anal, colon discomforts, infections or diseases. The reference discloses the kit having a rectal plug. However, the cited references differ from the present invention because they fail to disclose a device for hemorrhoid relief which generates biphasic electrotherapy pulses within a user's anus. The device includes a housing assembly including a battery and a communication module. The device further including a capsule assembly having three pole members. The device is enabled to connect to a user's mobile device in order to control parameters of the electrotherapy pulses.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a device for hemorrhoid relief that is inserted into a user's anus and generates biphasic electrotherapy pulses to reduce hemorrhoid inflammation.

It is another object of this invention to provide a device for hemorrhoid relief that includes parameters that can be wirelessly modified through a mobile device.

It is still another object of the present invention to provide a device for hemorrhoid relief that fits comfortably within a user's anus and provides electrotherapy.

It is still another object of the present invention to provide a device for hemorrhoid relief that can be easily recharged through wireless charging.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
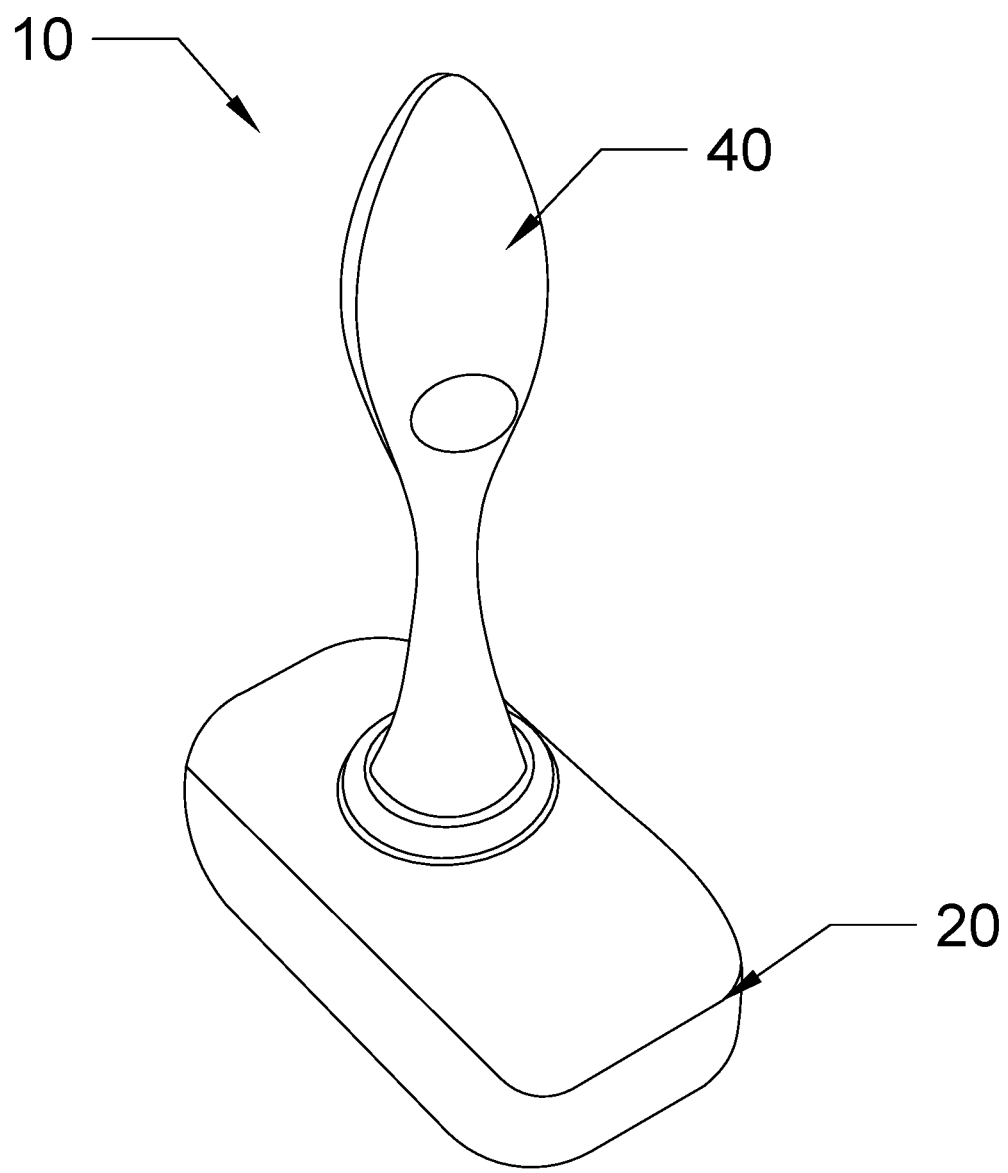
FIG. 1 represents an isometric view of hemorrhoid relief device 10 having housing assembly 20 and capsule assembly 40 in accordance to an embodiment of the present invention.
Figure 2:
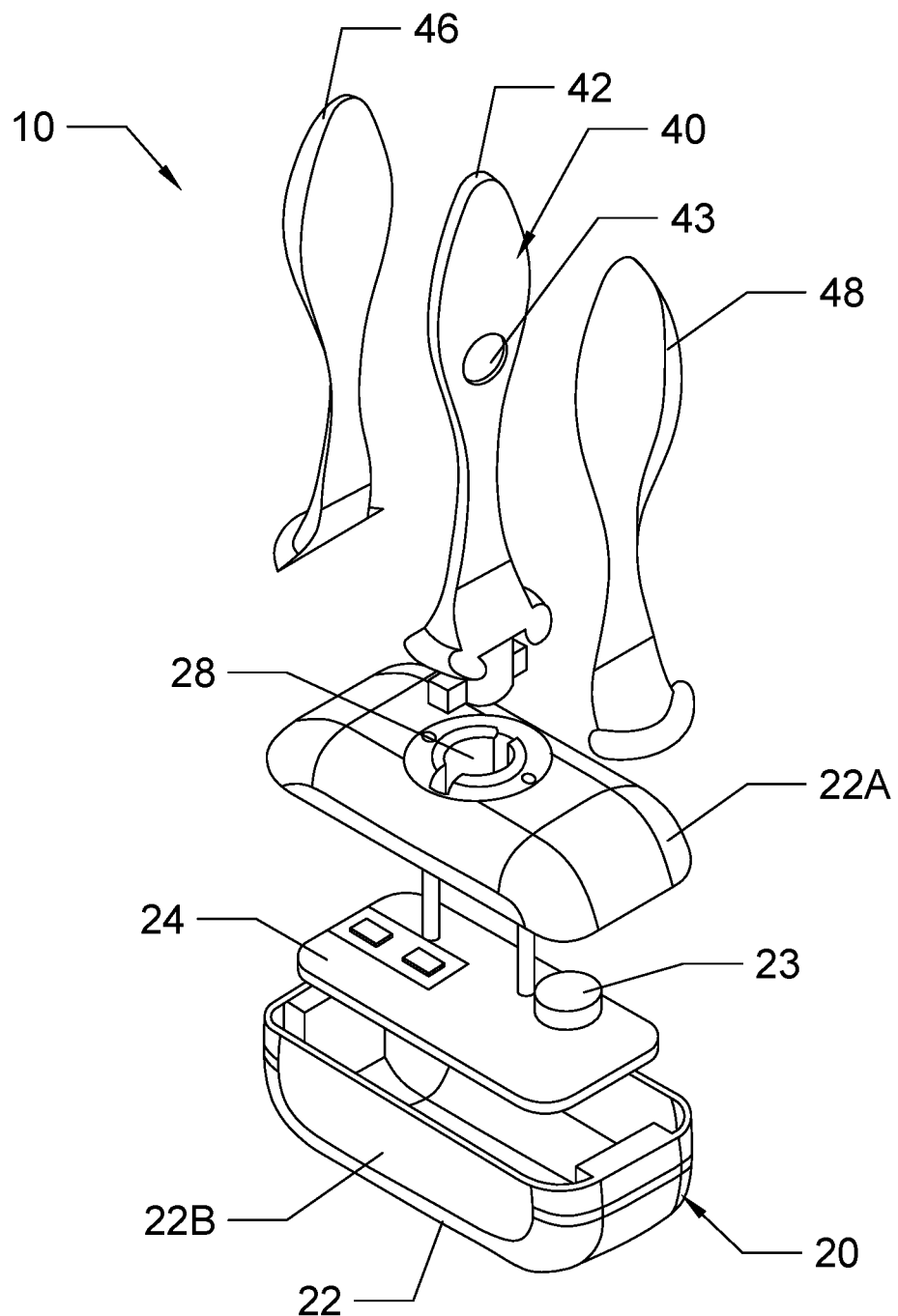
FIG. 2 shows an isometric exploded view of hemorrhoid relief device 10 depicting various internal components of housing assembly 20 and capsule assembly 40 in accordance to an embodiment of the present invention.
Figure 3:
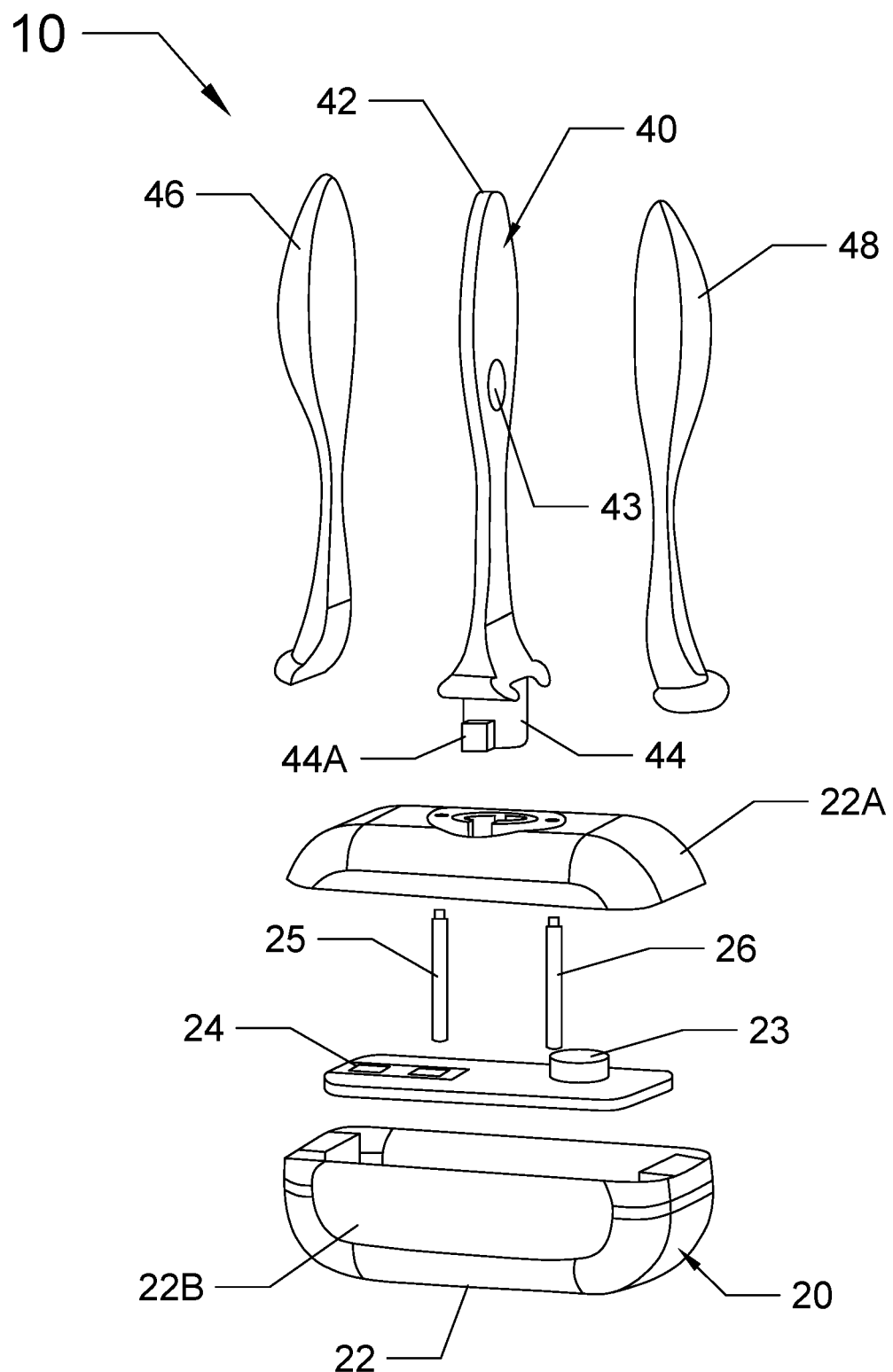
FIG. 3 illustrates another isometric exploded view of hemorrhoid relief device 10 depicting various internal components of housing assembly 20 and capsule assembly 40 in accordance to an embodiment of the present invention.
Figure 4:
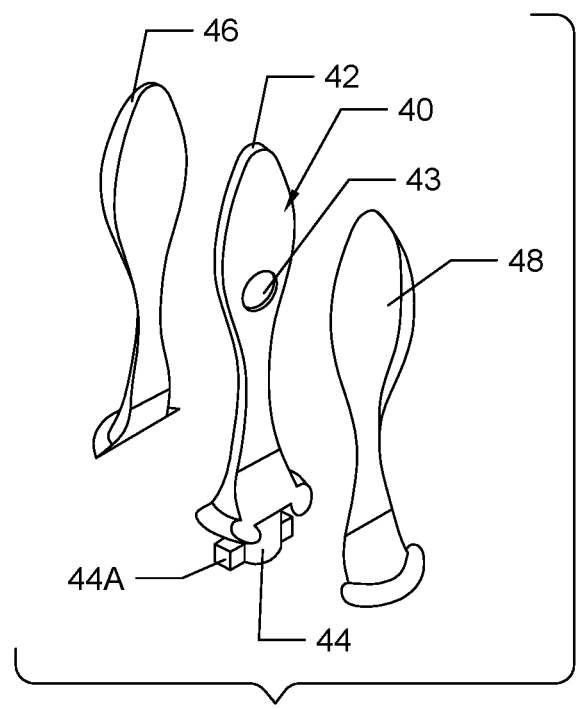
FIG. 4 is a representation of an isometric exploded view of capsule assembly 40 depicting plastic core 42, first pole 46, and second pole 48 in accordance to an embodiment of the present invention.
Figure 5:
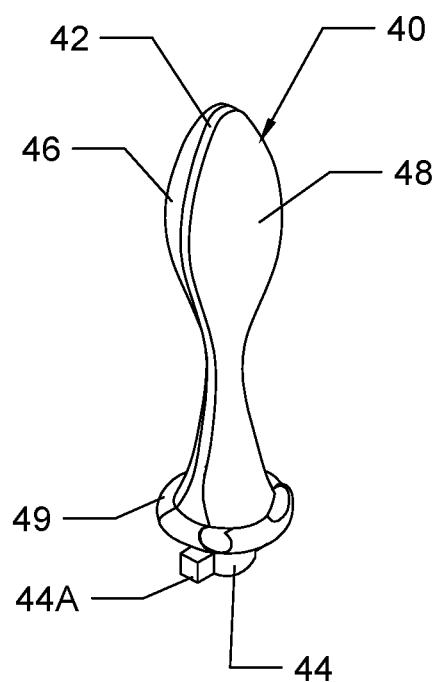
FIG. 5 shows an isometric view of capsule assembly 40 in an assembled configuration in accordance to an embodiment of the present invention.
Figure 6:
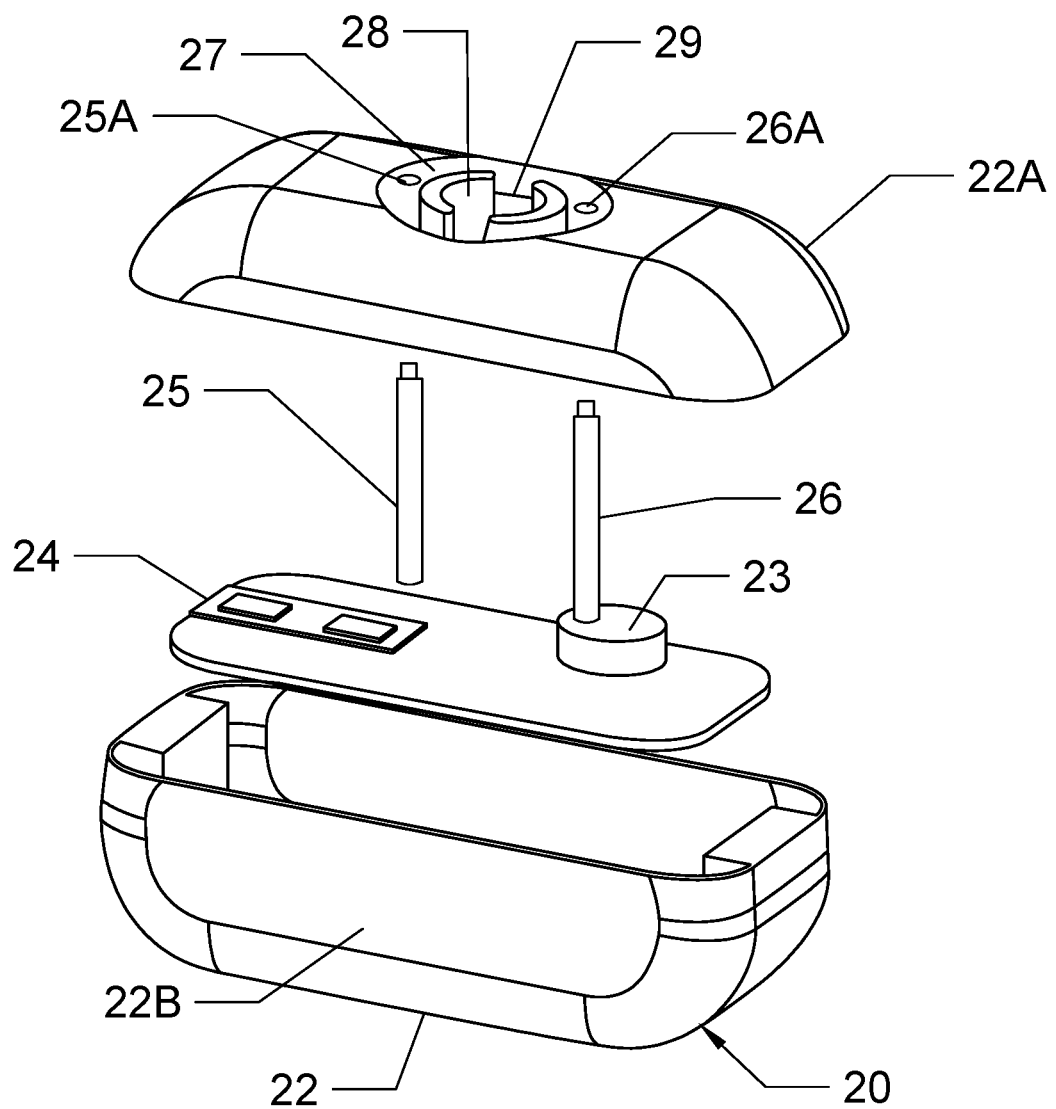
FIG. 6 illustrates an isometric exploded view of housing assembly 20 depicting internal components such as battery 23, anode rod 25, and cathode rod 26 in accordance to an embodiment of the present invention.
Figure 7:
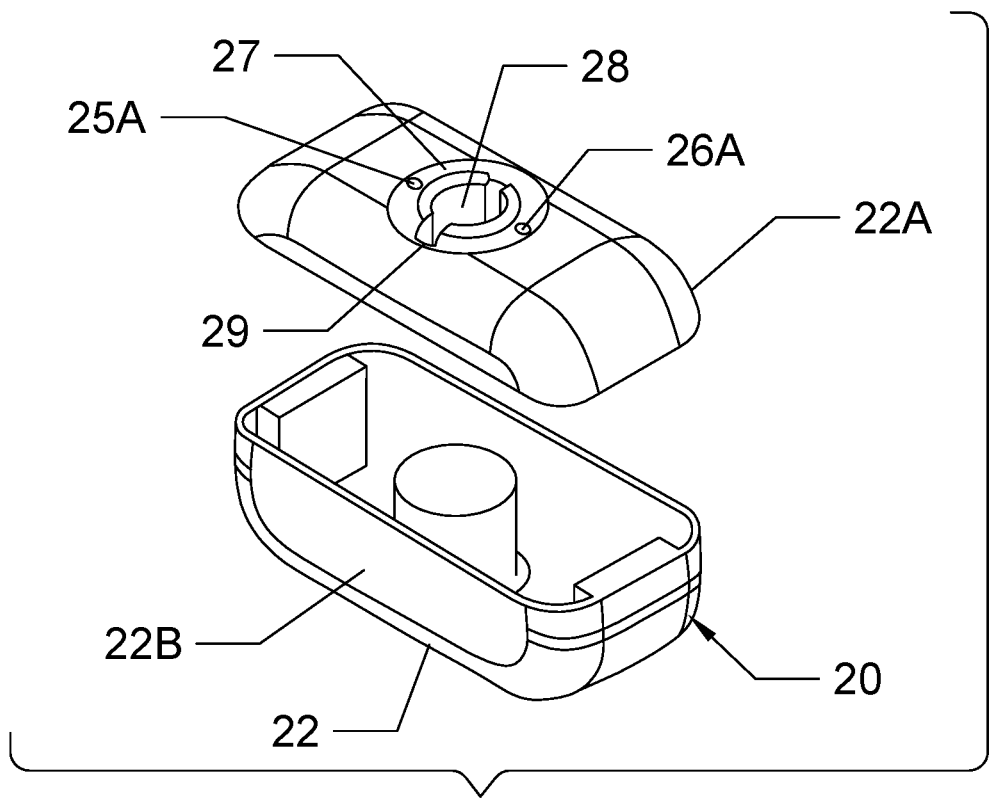
FIG. 7 represents an isometric exploded view of housing assembly 20 depicting top portion 22A and bottom portion 22B of a housing 22 in accordance to an embodiment of the present invention.
Figure 8:
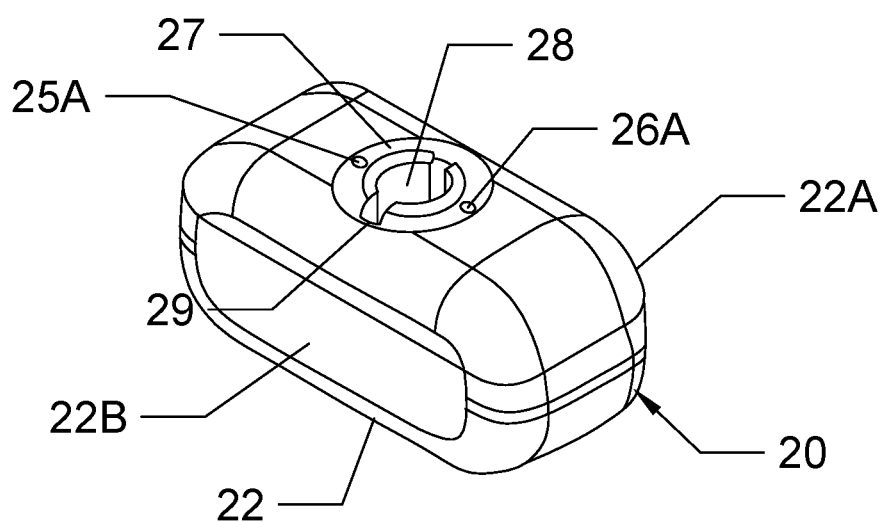
FIG. 8 shows an isometric view of housing assembly 20 depicting housing 22 in an assembled configuration in accordance to an embodiment of the present invention.

Referring now to the drawings, where the present invention is generally referred to with numeral 10, it can be observed a hemorrhoid relief device 10 that basically includes a housing assembly 20 and a capsule assembly 40.

Housing assembly 20 includes a housing 22 having a top portion 22A and a bottom portion 22B. In one embodiment, housing 22 may be provided in the shape of a curved substantially rectangular body or an oval shape. Additionally, housing 22 may be made of a durable plastic material. Top portion 22A may represent a top half of housing 22 that is removably coupled to bottom portion 22B. Housing 22 further contains an interior space that houses a battery 23 and a communication module 24. In one implementation, battery 23 may be provided as a CP1454 varta lithium battery or any other similar type of battery. Additionally, battery 23 may be configured to be a wireless rechargeable battery. As a result, a user may recharge hemorrhoid relief device 10 on a wireless charging pad for efficiency and easy of use. Other implementations may include battery 23 as a battery that is rechargeable through a wired means or a combination of wired and wireless means. In one embodiment, battery 23 may be provided on a printed circuit board that is housed within housing 22. Additionally, housing assembly 20 includes communication module 24 housed within housing 22. In one embodiment, communication module 24 is provided in a printed circuit board alongside battery 23. Communication module 24 may be provided in form of a microcontroller which allows a mobile device to communicate with hemorrhoid relief device 10 over a communication network. The mobile device may then enable a user to actuate an operate hemorrhoid relief device 10. In other embodiments, housing 22 may be provided with additional buttons for the operation of the device without the use of a mobile device. In one embodiment, this communication network may be provided as a Bluetooth communication link. Other embodiments may feature other wireless communication means such as LTE and WiFi communication systems. Communication module 24 then enables a user to control various parameters of hemorrhoid relief device 10 from a mobile device.

Housing assembly 20 further includes an anode rod 25 and a cathode rod 26 located within housing 22. Anode rod 25 and cathode rod 26 are provided as electrically charged rods that are charged through battery 23. In one embodiment, anode rod 25 and cathode rod 26 may be provided as metal cylindrical rods that extend within housing 22. Anode rod 25 represents a rod that receives positively charged ions from battery 23. Cathode rod 26 represents a rod that receives negatively charged ions form battery 23. In one implementation, anode rod 25 and cathode rod 26 are placed in a vertical position within housing 22. Furthermore, both anode rod 25 and cathode rod 26 extend through top portion 22A. Top portion 22A may have channel openings including an anode rod opening 25A and a cathode rod opening 26A located along a channel 27 which then receive the respective rods therethrough. This configuration creates a means for anode rod 25 and cathode rod 26 to communicate with capsule assembly 40. As a result of this assembly, capsule assembly 40 may then provide electrotherapy pulses within a user's anus for hemorrhoid relief.

Figure 9:
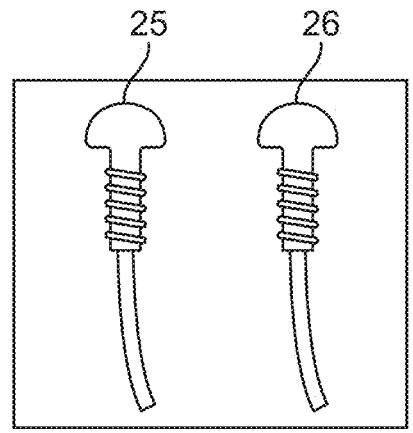
FIG. 9 illustrates an isometric view of anode rod 25 and cathode rod 26 provided in the form of an electrode having a wire in accordance to another embodiment of the present invention.
Figure 10:
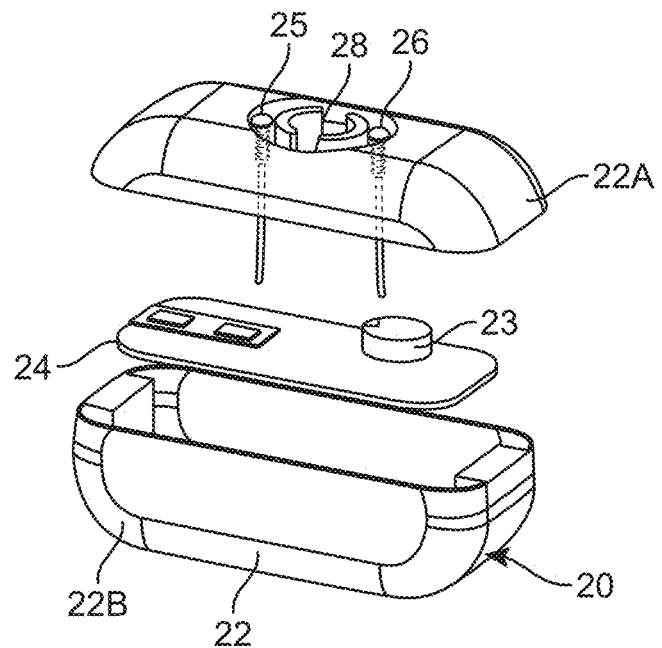
FIG. 10 is a representation of an isometric exploded view of housing assembly 20 implementing anode rode 25 and cathode rod 26 in an electrode form having wires in accordance to another embodiment of the present invention.

In another embodiment of the present invention, observed in FIGS. 9 and 10, anode rod 25 and cathode rod 26 may be provided in an electrode form having a wire. As observed in the figures, anode rod 25 and cathode rod 26 may be equipped with outer threads that are then received by inner threads located within an inner surface of anode rod opening 25A and cathode rod opening 26A. In another embodiment, anode rod 25 and cathode rod 26 may feature an electrode being absent of outer threads. In this embodiment, the electrode is securely pushed within anode rod opening 25A and cathode rod opening 26A. The electrode may be made of any suitable stainless-steel material or titanium which effectively transfer an electric charge. The electrodes are then provided with a wire that is mounted to the circuit board within housing 22. The wires then transfer an electric charge that is received by battery 23.

Housing assembly 20 further includes an opening 28 that is surrounded by channel 27 located on top portion 22A. In one implementation, opening 28 may be provided as having a circular shape and extends through top portion 22A. Additionally, opening 28 may be provided on a center position of top portion 22. Cannel 27 may then surround the circumference of opening 28. In one embodiment, channel 27 may be provided as a circular cavity within surrounds opening 28. Furthermore, channel 27 extends within top portion 22A a predetermined amount. Channel 27 creates a suitable cavity to receive capsule assembly 40 thereon. Opening 28 may further include slots 29 which may be placed at opposite ends of opening 28. In one implementation slots 29 may be provided as rectangular cut portions which extend from opening 28 to channel 27. Opening 28 and slots 29 provide a suitable mounting and securing means for capsule assembly 40 mounted thereon. Other embodiments of the present invention may feature other forms of securing means for housing assembly 20 and capsule assembly 40.

Capsule assembly 40 includes a plastic core 42 having a base member 44 attached to a bottom end. In one embodiment, plastic core 42 is provided as a flat, two-sided plastic member. Plastic core 42 may further include a shape that features a concave section and a convex section. The concave section may be provided near a bottom portion of plastic core 42. Furthermore, the convex section may be provided near a top portion of plastic core 42. The convex section may resemble and oval like shape. Plastic core 42 may further include a cavity 43 provided on each side of the two-sided plastic member. In one implementation, cavity 43 may be provided as a circular opening which partially extends into a thickness of plastic core 42. Additionally, cavity 43 may be located on the convex section of plastic core 42. Base member 44 may be provided as an integral or removable component of plastic core 42. Furthermore, base member 44 may be provided as having a cylindrical shape. In one embodiment, the radius of base member 44 is a radius that cooperates with the radius of opening 28. Base member 44 may further include locking members 44A that are then received by slots 29 when base member 44 in inserted within opening 28. Locking members 44A may be provided as rectangular members placed at opposite ends of base member 44 that cooperate with the shape and position of slots 29. This configuration provides a secure attachment and locking means for capsule assembly 40 onto housing assembly 20.

Capsule assembly 40 further includes a first pole 46 and a second pole 48 that are coupled to plastic core 42. In one embodiment, first pole 46 and second pole 48 are made of an electric conductive silicon material. This material allows first pole 46 and second pole 48 to receive and electrical charge and become charged poles. Plastic core 42 then serves as a neutral member that does not receive charge due to its plastic nature. In one embodiment this plastic material may be provided as HD-PE (high density polyethylene) or UHMW-PE (ultra-high molecular weight polyethylene). First pole 46 and second pole 48 may be provided in a shape that cooperates with the shape of plastic core 42. As a result, first pole 46 and second pole 48 may also include a concave section and a convex section to match plastic core 42.

Furthermore, first pole 46 and second pole 48 may each include a flat side that is received by plastic core 42 and a rounded side that faces outwardly. In one implementation, first pole 46 and second pole 48 are each made and formed through an injection molding process. During this process a liquid form of the electric conductive material is poured into a mold containing plastic core 42. As the liquid forms and solidifies within the mold, the liquid form of the material occupies cavity 43. The electric conductive materiel is then hardened and securely coupled to plastic core 42 to form a single pole that is to be inserted into a user's anus. A lip portion 49 is then formed along the bottom end of this unitary pole. Lip portion 49 may be provided as a circular protruding ring that cooperates with the shape of channel 27. Once base member 44 is inserted within opening 28, lip portion 49 is then received by channel 27 and sits comfortable thereon.

Once capsule assembly 40 is mounted onto housing assembly 20, first pole 46 and second pole 48 are then configured to receive an electrical charge. Anode rod 25 and cathode rod 26 are then exposed through anode rod opening 25A and cathode rod opening 26A and are now in contact with first pole 46 and second pole 48 respectively. As a result, anode rod 25 carrying the positively charged ions from battery 23 are then distributed to first pole 46 to then effectively positively charge the pole. Furthermore, cathode rod 26 carrying negatively charged ions from batter 23 are then distributed to second pole 48 to effectively negatively charge the pole. This configuration then allows hemorrhoid relief device 10 to generate and provide biphasic electrotherapy pulses when inserted into a user's anus.

In one implementation, hemorrhoid relief device 10 generates biphasic electrotherapy pulses having several modes. The modes provide a positive rectangular pulse (tp) followed by a negative rectangular pulse (tn) that may each last between 250 μs and 125 μs, ideally with a curve less than 10% through 5%. Additionally, a gap or transition time is provided between the positive and negative pulses that are half the width of the pulses. Furthermore, the pulse width and intensity of the positive and negative pulses may vary between five volts and eighty volts. The device may further operate with a timer that includes time periods varying between five minutes and sixty minutes. In one mode of operation, a user may have the ability of selecting a mode where there is a frequency modulation. This allows a user to vary the idle times of the rectangular pulses. In another mode of operation, a user may have the ability of selection a mode where there is a modulation in intensity not greater than a difference between a minimum pulse and a maximum pulse at ten volts. In yet another mode of operation, a user may be provided with three sets of positive and negative pulses with a rest time of 20 ms and then a rest time of 460 ms to the next pulse train. In yet another mode of operation, a user may be provided with a positive and negative pulse train with a resting time of 15 ms with a duration of the pulse being 3 s followed by a positive and negative pulse train with a rest time of 500 ms and a duration of 3 s. In one implementation, a user may edit various parameters mentioned above by connecting hemorrhoid relief device 10 with a mobile device through a Bluetooth connection. This allows a user to cater the electrotherapy pulses to their needs. Additionally, hemorrhoid relief device 10 may also include a status indicator which may be provided in the form of an LED which indicates that the battery is being charged and another status indicator which indicates when the battery is in a low power status.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device for the relief of hemorrhoid inflammation, comprising:
   a. a housing assembly housing a circuit board having a battery, a communication module, and charged rods, said housing assembly having an opening, wherein said housing assembly includes a top portion and a bottom portion, said opening located on said top portion, said circuit board located between said top portion and said bottom portion; and
   b. a capsule assembly including a core member having a first pole and a second pole coupled to said core member, wherein the core member, the first pole and the second pole each have substantially the same length and shape, said core member located entirely between the first pole and the second pole, wherein a base member includes locking members thereon, said base member and said locking members are all located entirely below the core member, wherein said base member and said locking members are entirely below said first pole and said second pole, wherein said core member, said first pole and said second pole each have a width that does not extend past the periphery of said housing assembly, wherein said first pole and said second pole are in abutting engagement with a top surface of said housing assembly, wherein said first pole and said second pole each include an inner surface that is evenly flush and abutting with outer sides of the core member, said first pole and said second pole being in contact with said housing assembly and said charged rods to create electrically charged poles, wherein said electrically charged poles provide electrotherapy pulses, said capsule assembly configured to be inserted within a user's anus to provide said electrotherapy pulses to relieve said user from hemorrhoid inflammation, wherein said base member with said locking members thereon is attached to a bottom end of said core member, said core member with said base member attached is mounted within said opening of said housing assembly.

2. The device for the relief of hemorrhoid inflammation of claim 1 wherein said charged rods are provided in an electrode form having wires connected to said circuit board.

3. The device for the relief of hemorrhoid inflammation of claim 1 wherein said opening is surrounded by a channel, wherein said channel is a substantially circular ring channel structure that is recessed into the top portion, wherein said core member, said first pole and said second pole sits flush within the channel when mounted to the housing.

4. The device for the relief of hemorrhoid inflammation of claim 3 wherein said top portion includes slots located on opposite ends of said opening and extend into said channel.

5. The device for the relief of hemorrhoid inflammation of claim 4 wherein said slots break up said opening into two identical curved portion which assist in securing said base member within said opening.

6. The device for the relief of hemorrhoid inflammation of claim 3 wherein said channel includes charged rod openings that allow for electricity to pass from said charged rods to said first and second poles.

7. The device for the relief of hemorrhoid inflammation of claim 1 wherein said first pole and said second pole each include an outer concave section and an outer convex section.

8. The device for the relief of hemorrhoid inflammation of claim 1 wherein said core member includes a cavity on each outer side of said core member.

9. The device for the relief of hemorrhoid inflammation of claim 1 wherein said first pole entirely covers a first side surface of said core member and said second pole covers entirely covers a second side surface of said core member.

10. The device for the relief of hemorrhoid inflammation of claim 1 wherein a mobile device communicates with said device through said communication module over a Bluetooth connection.

11. The device for the relief of hemorrhoid inflammation of claim 10 wherein said mobile device includes a software that allows a user to modify various parameters of said device.

12. The device for the relief of hemorrhoid inflammation of claim 1 wherein said core member, said first pole, and said second pole when combined form a lip portion at said bottom end.

13. The device for the relief of hemorrhoid inflammation of claim 1 wherein said base member is cylindrical and wherein said locking members are rectangular.

14. The device for the relief of hemorrhoid inflammation of claim 1 wherein distal lateral ends of said top portion slope downwards, and distal lateral ends of said bottom portion slope upwards.

\* \* \* \* \*